United States Patent [19]

Viesturs et al.

[11] 4,372,318

[45] Feb. 8, 1983

[54] THERMAL TREATMENT DEVICE

[76] Inventors: Eric Viesturs, 680B Heritage Village; Gundar Viesturs, Oakhill Dr., both of Southbury, Conn. 06488

[21] Appl. No.: 203,988

[22] Filed: Nov. 4, 1980

[51] Int. Cl.$^3$ .............................................. A61F 7/00
[52] U.S. Cl. .................................. 128/403; 128/399; 128/402
[58] Field of Search ...................... 128/399, 402, 403; 150/2.1–2.7, 3, 7; 229/62

[56] References Cited

U.S. PATENT DOCUMENTS

| | | | |
|---|---|---|---|
| 2,288,745 | 7/1942 | Sammis | 128/403 X |
| 2,796,903 | 6/1957 | Gazelle | 150/2.3 |
| 3,173,419 | 3/1965 | Dubilier et al. | 128/402 X |
| 3,217,934 | 11/1965 | Schneider et al. | 229/62 X |
| 3,224,640 | 12/1965 | Schneider et al. | 229/62 X |
| 3,463,161 | 8/1969 | Andrassn | 128/402 |
| 3,736,769 | 6/1973 | Peterson | 128/402 X |

FOREIGN PATENT DOCUMENTS

1511723  1/1967  France .................................. 128/402

*Primary Examiner*—Kyle L. Howell
*Assistant Examiner*—John C. Hanley

[57] ABSTRACT

A thin flexible member, vertically elongated and hollow, has a rear surface and an oppositely disposed exposed front surface. The member has top and bottom edges and oppositely disposed side edges. The front surface has a slit communicating with the interior of the member which extends between the side edges thereof adjacent but below the top edge thereof. A horizontally elongated flexible strip extends across said member intermediate the top and bottom edges thereof and adjacent the front surface. The strip is secured to the side edges and is otherwise spaced from the front surface. The top portion of the member above the strip can be folded upon the remaining portion of said member and extend through the space between the strip and the member with the slit being disposed below the strip to seal the interior of the member. A flexible cushioning layer can be secured to the rear surface of the member. Alternatively, the member can have a rear pocket in which the cushioning layer can be removably disposed.

Two such members can be suitably interconnected to form a structure particularly adapted for thermal treatment of eyes.

1 Claim, 4 Drawing Figures

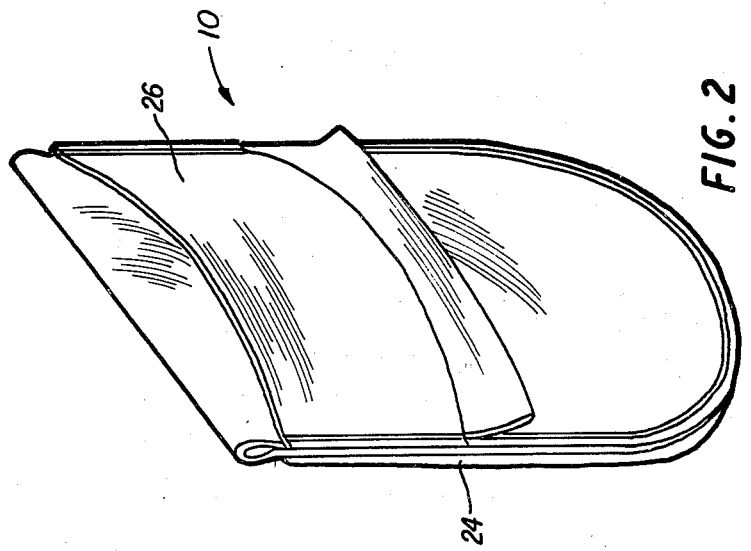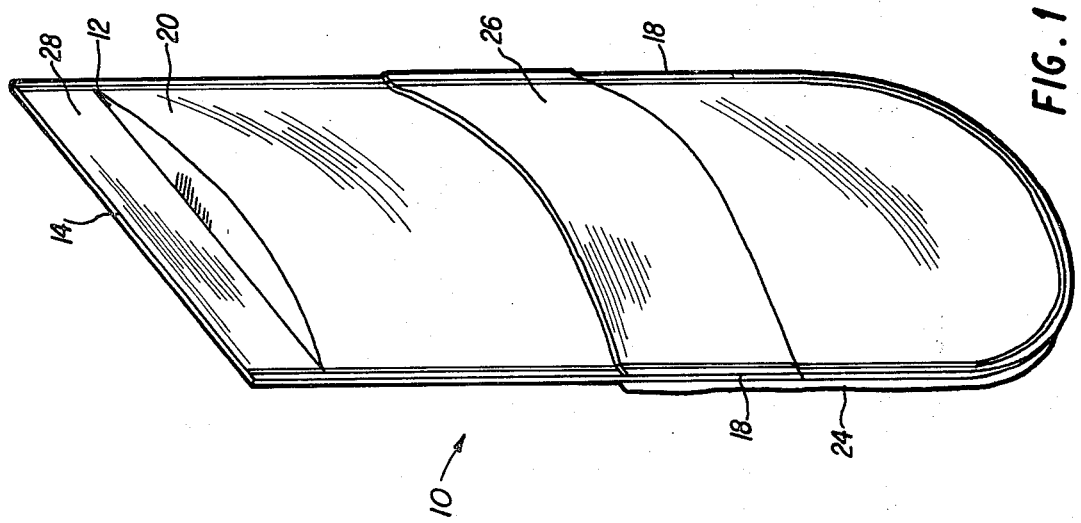

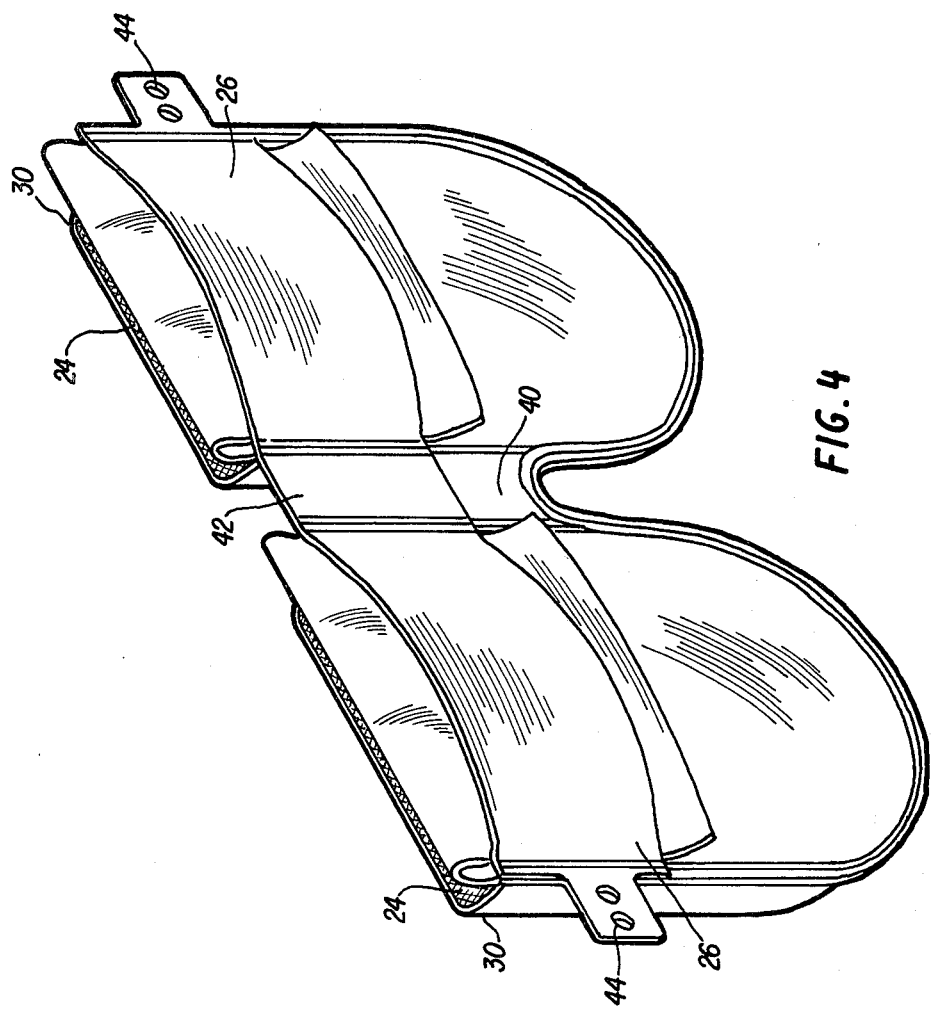
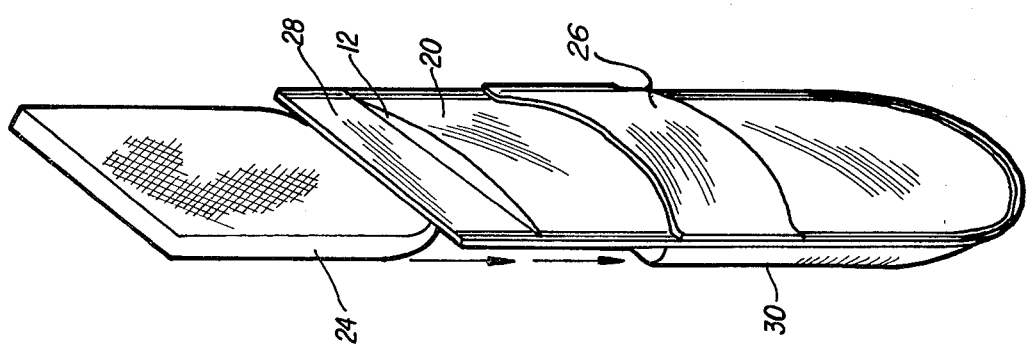

THERMAL TREATMENT DEVICE

BACKGROUND OF THE INVENTION

Patients recovering from surgery or being otherwise treated for a variety of conditions often have to have hot or cold compresses applied externally. A variety of therapeutic devices adapted to supply the desired thermal treatment are know to the art.

This invention is directed toward a new type of therapeutic device which is not only inexpensive and disposable, but also is provided with simple means for permitting the hot or cold material used for thermal treatment to be easily and quickly removed or inserted as well as being retained in a leakproof manner. Moreover, the conventional devices when placed in contact with selected portions of the body bring same up to the required elevated or lowered temperature almost immediately whereby the thermal shock is often unpleasant and causes the patient discomfort. The present invention incorporates thermal delay means which enables the patient to avoid thermal shock; the body portions being treated are gradually subjected to the elevated or lowered temperature so that the rate of change of temperature with time is sufficiently slow to minimize the discomfort.

SUMMARY OF THE INVENTION

In accordance with the principles of this invention, there is provided a therapeutic device adapted to be placed removably over a selected portion of the body of a patient. This device includes a thin flexible member which is hollow and is vertically elongated. The member has a rear surface adapted to be disposed adjacent the eye portion of the body to be treated and has an oppositely disposed front surface adapted to be exposed. The member has top and bottom edges and oppositely disposed side edges. The front surface has a slit communicating with the interior of the member and extending between the side edges thereof adjacent but below the top edge thereof.

A horizontally elongated flexible strip extends across said member adjacent the front surface intermediate the top and bottom edges thereof. The strip is secured to the member in spaced apart discrete positions adjacent the side edges and is otherwise spaced from the front surface. The top portion of the member above the strip is adapted to be folded or rolled up upon the remaining portion of the member and to extend through the space between the strip and the member with the slit being disposed below the strip to seal the interior of the member.

Thus heated material such as hot water or a cold material such as a mixture of ice and cold water can be introduced into the interior of the member via the slit and the top portion can be folded as indicated to form a leakproof seal. The top portion can be easily unfolded to enable the hot or cold material to be removed easily.

When the rear surface of the member is placed directly in contact with the portion of the body being treated, the rate of transfer of the elevated or lowered temperature of the material in the member to the body is essentially instantaneous whereby the patient can suffer considerable discomfort. To avoid thermal shock, the rear surface of the member can be covered with a flexible cushioning layer which is interposed between the section and the body. This layer does not heat up or cool immediately, but does so gradually whereby the body portion is gradually heated or cooled and patient discomfort is minimized.

Two such members can be interconnected by a suitably thin and narrow element to form a therapeutic device particularly adapted for eye treatment as explained in more detail hereinafter.

BRIEF DESCRIPTION OF THE DRAWINGS

FIG. 1 is a perspective view of one form of the invention in open position.

FIG. 2 is a similar view shown in closed position.

FIG. 3 is a view similar to FIG. 1; but showing a modification thereof.

FIG. 4 is a perspective view of another embodiment of the invention.

DETAILED DESCRIPTION OF PREFERRED EMBODIMENTS

Referring now to FIGS. 1 and 2, there is shown a thin flexible plastic member 10 which is transparent. This member typically can be formed of polypropelene having a wall thickness of 0.005 inches. The member has a top horizontal edge 14, a bottom curved edge and opposite vertical side edges 18. These sections can each approximate a rectangle 4.375 inches wide and 8.25 inches long.

The member has a horizontal slit 12 in the front surface 20 thereof which extends between edges 18 adjacent but below the top edge. That portion of the rear surface 22 of the member extending between the bottom edge and strip 26 is covered by a flexible cushioning layer 24, typically formed of styrofoam about 0.25 inches thick. This layer 24 minimizes thermal shock as previously described.

A vinyl strip 26 which is flexible and horizontally elongated typically two inches wide and 0.125 inches thick extends across the front surfaces of the member intermediate the top and bottom edges thereof.

The strip is secured to the member in spaced apart positions adjacent the side edges and is otherwise spaced from the front surface. The top portion of the member above the strip is adapted to be folded or rolled up upon the remaining portion of the member (after hot or cold material is inserted via the slit into this remaining portion) and thereafter to extend through the space between the strip and the section as a seal.

The front portion of the member between the top edge and the slit can be covered with another vinyl strip 28 to facilitate folding.

As shown in FIG. 3, a thin flexible sheet 30 of the same material as member 10 can be secured along its periphery to that portion of the periphery of the rear surface which lies below the top edge of strip 26. The sheet 30 has a top horizontal edge spaced from the rear surface except at the side edges and aligned with the top horizontal edge of the strip, thus forming a pocket. A flexible cushioning layer 24 can be removably disposed in the pocket.

FIG. 4 shows two of the members of FIG. 1 disposed side by side in coplanar relationship with aligned front surfaces and joined by an elongated central element 40 of the same material as member 10. This element is secured at each vertical edge to the adjacent side edge of the corresponding member. The vinyl strips 26 can be made integral by a central addition 42 overlying and secured to the front surface of element 40. Opposite ends of the integral strip can extend beyond the opposite side edges of the members and can have holes 44.

The resultant structure can be used for therapeutic treatment of the eyes, with each member overlying a corresponding eye, and element 40 overlying the nose. Strips or other means can engage the holes 44 to secure the device detachably to the head of a patient.

Each member can be constructed as shown in FIG. 1 with a layer 24 secured to the rear surface or as shown in FIG. 3 with a rear pocket and with a layer 24 removably disposed in the pocket.

As previously stated above, the top portion of the member can be folded or rolled up upon the remaining portion of the member. In the claims which follows, the term folded has been used for convenience to describe both folded and rolled up conditions.

We claim:

1. A device used to overlie the eyes and nose of patient receiving thermal treatment, said device comprising:

first and second like thin flexible vertically elongated hollow interior members adapted to receive hot or cold material, each member having oppositely disposed front and rear surfaces, top and bottom edges and oppositely disposed side edges defining said interior, the front surface of each member having a slit communicating with each respective interior of the member to enable insertion or removal of hot or cold material into said interior of each member, each slit extending between the side edges of its corresponding front member adjacent but below the top edge of each front member;

a thin vertically elongated flexible central element having oppositely disposed front and rear surfaces and itself disposed between the first and second members, said element having first and second oppositely disposed side edges, each of the first and second side edges of the element being connected to an adjacent side edge of a corresponding one of said first and second members; and a horizontal elongated flexible strip extending across the front surfaces of said first and second members and said element between the top and bottom edges of said first and second members, the strip having a top edge disposed below the slits of the first and second members, said strip being secured to each member in spaced apart discrete positions adjacent the side edges of each front member and being otherwise spaced from the front surface of each member, each member having a top portion which is disposed above the top edge of the strip and which can be folded upon the remaining portion of the member and positioned between the strip and the front surface of the member to seal said slit, each top portion when folded having a horizontal line of fold coincident with the top edge of said strip;

first and second thin flexible sheets, each sheet being disposed adjacent the rear surface of the corresponding member and sealed thereto along the bottom edge and along those parts of the side edges which are disposed below the top edge of the strip, the top edge of each sheet being aligned with the top edge of the strip, thus forming a pocket whereby each of the first and second members has a corresponding pocket; and first and second flexible cushioning layers having thermal delay characteristics, each of the layers being removably disposed in the pocket of the corresponding one of said members.

* * * * *